United States Patent
Satake

(10) Patent No.: US 6,491,710 B2
(45) Date of Patent: Dec. 10, 2002

(54) BALLOON CATHETER FOR PULMONARY VEIN ISOLATION

(76) Inventor: Shutaro Satake, 4-8-18, Kamakurayama, Kamakura-Shi, Kanagawa-Ken (JP)

( * ) Notice: Subject to any disclaimer, the term of this patent is extended or adjusted under 35 U.S.C. 154(b) by 194 days.

(21) Appl. No.: 09/750,108

(22) Filed: Dec. 29, 2000

(65) Prior Publication Data

US 2002/0029062 A1 Mar. 7, 2002

(51) Int. Cl.⁷ .............................................. A61M 29/00
(52) U.S. Cl. ....................................... 606/191; 604/96
(58) Field of Search .................................. 606/191, 192, 606/193, 196, 198

(56) References Cited

U.S. PATENT DOCUMENTS

| | | | |
|---|---|---|---|
| 5,344,398 A | * 9/1994 | Hara | 604/21 |
| 5,609,591 A | * 3/1997 | Daikuzono | 604/21 |
| 5,766,192 A | * 6/1998 | Zacca | 606/159 |
| 5,902,268 A | * 5/1999 | Saab | 604/113 |
| 6,336,934 B1 | * 1/2002 | Gilson et al. | 606/159 |
| 6,413,273 B1 | * 7/2002 | Baum et al. | 623/1.19 |

\* cited by examiner

*Primary Examiner*—Kevin T. Truong
*Assistant Examiner*—Victor Nguyen
(74) *Attorney, Agent, or Firm*—Wenderoth, Lind & Ponack, L.L.P.

(57) ABSTRACT

A balloon catheter is capable of forming a transmural necrotic layer around the pulmonary vein ostium without excessively cauterizing the endocardium and of cauterizing portions of the four pulmonary veins around the ostium of the same one by one. The balloon catheter comprises: a catheter shaft consisting of a tubular outer shaft (2) and a tubular inner shaft (2), an inflatable balloon (4) capable of coming into contact with a predetermined annular portion of the entrance (20) of a pulmonary vein when inflated, a radio-frequency electrode (8) paired with a counter electrode (44) placed on the surface of a patient's body to transmit radio-frequency power, and placed in a wall forming the balloon (4) or in the balloon (94), a lead wire (12) electrically connected to the radio-frequency electrode (8), a cooling means (38) for pouring cooling liquid (36) to cool respective interior of the catheter shaft and the balloon (4), and a temperature sensor (14) for measuring temperature in the balloon (4).

12 Claims, 5 Drawing Sheets

BALLOON CATHETER FOR PULMONARY VEIN ISOLATION

BACKGROUND OF THE INVENTION

1. Field of the Invention

The present invention relates to a balloon catheter for pulmonary vein isolation and, more particularly, to a balloon catheter for atrium ablation for the treatment of a local lesion through local radio-frequency heating under pressure to treat atrial fibrillation.

2. Description of the Related Art

A known radio-frequency ablation method of electrically isolating a pulmonary vein repeats cauterization ten and some odd times to cauterize spots around the pulmonary vein successively with a catheter provided with metallic electrodes having 4 mm chips for the electric cauterization of the spots around the pulmonary vein. Most operations by this radio-frequency ablation method result in failure because the radio-frequency ablation method requires skilled catheter operation and is technically very difficult to achieve.

A radio-frequency ablation method of electrically isolating a pulmonary vein by radio-frequency heating using an inflatable balloon catheter is disclosed in Japanese Patent No. 2574119 issued to the applicant of the present invention.

The metallic electrodes having rough surfaces of the known catheter are exposed to blood. When the temperature of the electrodes is increased beyond a critical point by radio-frequency heating, thrombi are formed on the surfaces of the metallic electrodes. Therefore, a complication of thromboembolism arises when cauterization is repeated many times. The cauterization of many points one at a time takes a long time, which entails the hazard of exposure to radiation by x-ray fluoroscopy.

The radio-frequency ablation method disclosed in Japanese Patent No. 2574119 uses a large balloon capable of entirely occupying a right atrium to cover the ostium of all the four pulmonary veins. Therefore, the heart must be stopped temporarily and extracorporeal circulation must be effected by an artificial heart-lung apparatus.

SUMMARY OF THE INVENTION

Accordingly, it is an object of the present invention to solve those problems in the prior art and to provide a balloon catheter capable of forming a transmural necrotic layer around the pulmonary vein ostium without excessively cauterizing the endocardium and without forming thrombi, of cauterizing portions of the four pulmonary veins around the ostium of the same one by one and of achieving pulmonary vein isolation without requiring extracorporeal circulation.

Most causes of atrial premature beat that triggers atrial fibrillation, i.e., a kind of arhythmia, reside in the pulmonary vein. It has been recently found that atrial fibrillation can be prevented by electrically isolating those causes. The applicant of the present invention has developed various balloon catheters for radio-frequency heating, such as those disclosed in Japanese Patent Nos. 2538375, 2510428 and 2574119. Those patented balloon catheters are capable of easily cauterizing the inner surface of the pulmonary vein. Experimental data obtained by the applicant of the present invention showed that there is the possibility that those balloon catheters cause the restenosis of the pulmonary vein, entailing pulmonary hypertension. Therefore, the inventors of the present invention thought of a balloon catheter for pulmonary vein isolation without restenosis of pulmonary vein by circumferential ablation of the junction between the pulmonary vein and a left atrium, and the left atrium around the pulmonary vein.

To achieve the foregoing object, according to one aspect of the present invention, a balloon catheter for pulmonary vein isolation comprises: a catheter shaft consisting of a tubular outer shaft and a tubular inner shaft; an inflatable balloon, which has a larger diameter than that of the pulmonary vein ostium capable of contact with a predetermined annular portion of pulmonary vein ostium when inflated and having one end portion connected to the extremity of the tubular outer shaft and the other end portion connected to the extremity of the tubular inner shaft; a radio-frequency electrode paired with a electric plate placed on the surface of the patient's body to transmit radio-frequency power and placed in a wall forming the balloon or in the balloon; a lead wire connected to the radio-frequency electrode; a cooling means for pouring cooling liquid to cool the respective interior of the catheter shaft and the balloon; and a temperature sensor for measuring temperature in the balloon.

Preferably, the balloon as inflated has a shape resembling an onion having a larger diameter than that of pulmonary vein ostium on the side of the tubular outer shaft of the catheter shaft.

Preferably, the balloon as inflated has a shape resembling a mushroom having a larger diameter than that of pulmonary vein ostium on the side of the tubular outer shaft of the catheter shaft.

Preferably, the radio-frequency electrode is wound round the tubular inner shaft of the catheter shaft.

Preferably, the radio-frequency electrode is formed in a circular shape on the inner surface of the wall of the balloon so as to be located close to the predetermined portion when the balloon is inflated.

Preferably, the predetermined portion is the junction between the pulmonary vein and the left atrial wall.

Preferably, the predetermined portion is a portion of the left atrial wall around a pulmonary vein.

Preferably, the cooling means circulates cooling liquid.

Preferably, a U-shaped cooling liquid passage through which the cooling liquid can be circulated is formed in the tubular inner shaft of the catheter shaft.

Preferably, radio-frequency power is supplied to the radio-frequency electrode to heat the balloon at a predetermined temperature and the temperature of the balloon is monitored by means of the temperature sensor.

Preferably, radio-frequency power is supplied to the radio-frequency electrode so that impedance between the radio-frequency electrode and the electric plate is in a predetermined impedance range and the impedance between the radio-frequency electrode and the electric plate is monitored.

Preferably, the tubular outer shaft, the tubular inner shaft and the balloon are formed of an antithrombotic resin and have smooth surfaces, respectively.

Since the balloon is capable of coming into contact with the predetermined annular portion of a pulmonary vein ostium when inflated, the annular portion of the of each pulmonary vein ostium can be individually cauterized without requiring extracorporeal circulation. Since the respective interiors of the catheter shaft and the balloon can be cooled, the excessive heating of the catheter shaft by the lead wire and the radio-frequency electrode and the resultant deformation of the catheter shaft can be prevented. Since the temperature of the interior of the balloon is measured by the temperature sensor, a transmural necrotic layer can be formed without excessively cauterizing the endocardium.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Figure 1:
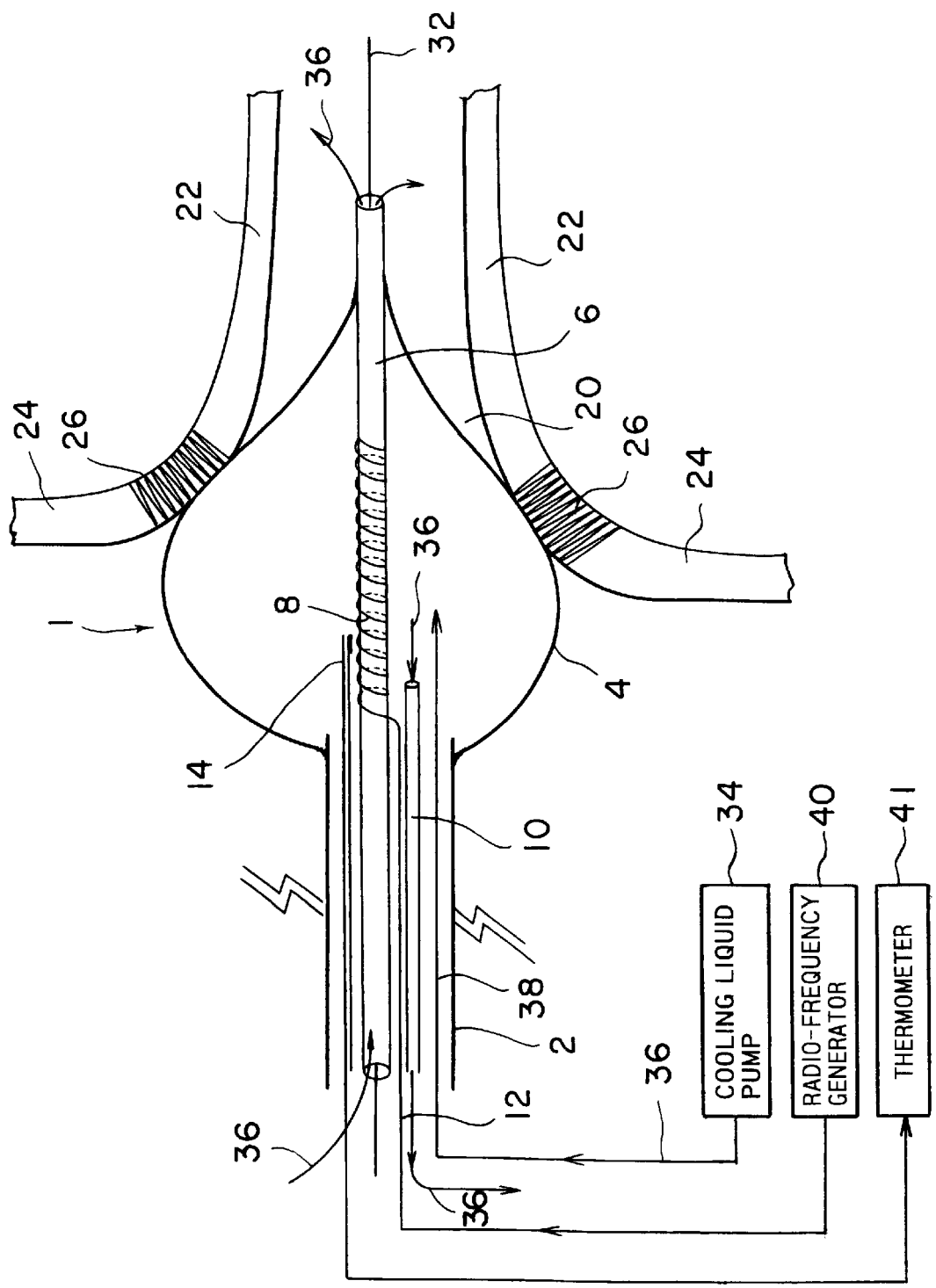
FIG. 1 is schematic sectional view of a balloon catheter for pulmonary vein isolation in a first embodiment according to the present invention in a state where a balloon is inflated.

Referring to FIG. 1 showing a balloon catheter 1 in a first embodiment according to the present invention for pulmonary vein isolation, the balloon catheter 1 includes a catheter shaft consisting of a tubular outer shaft 2 and a tubular inner shaft 6 coaxially inserted in the tubular outer shaft 2, an inflatable balloon 4 having one end portion connected to the extremity of the tubular outer shaft 2 and the other end portion connected to the extremity of the tubular inner shaft 6, a radio-frequency electrode 8 placed in the balloon 4, a lead wire 12 electrically connected to the radio-frequency electrode 8, a vent tubular shaft 10 for pouring cooling liquid into the balloon 4 for cooling, and a thermocouple 14 placed in the balloon 4 to measure the temperature of the interior of the balloon 4. A guide wire 32 can be extended through the tubular inner shaft 6. Cooling water 36 can flow through the tubular inner shaft 6.

The balloon 4 is formed of an antithrombotic resin, such as Teflon (polytetrafluoroethylene), that has a smooth outer surface. As shown in FIG. 1, the balloon 4 as inflated has a shape resembling an onion having a larger portion on the side of the tubular outer shaft 2 of the catheter shaft. The balloon 4 as inflated is capable of coming into contact with a predetermined portion of the wall of a pulmonary vein 22 defining an ostium 20, such as an annular portion of the junction 26 between the pulmonary vein 22 and the left atrial wall 24.

A wire is wound in coils around a portion of the tubular inner shaft 6 extending in the balloon 4 to form the radio-frequency electrode 8. The guide wire 32 is inserted in the tubular inner shaft 6. Saline as cooling liquid 36 is supplied through an upper portion into the tubular inner shaft 6 and is discharged outside from the patient's body through a lower portion. The tubular inner shaft 6 heated by the radio-frequency electrode 8 formed on the outer surfaces of the tubular inner shaft 6 can be cooled by the cooling liquid 36.

The tubular outer shaft 2, similarly to the balloon 4, is formed of an antithrombotic resin and has a smooth surface.

A cooling liquid passage 38 is formed between the tubular outer shaft 2 and the tubular inner shaft 6. The cooling liquid 36 is supplied through the cooling liquid passage 38 into the balloon 4 by a cooling liquid pump 34 to cool the interior of the balloon 4. The cooling liquid 36 supplied into the balloon 4 and used for cooling the interior of the balloon 4 is discharged through the vent tubular shaft 10 extended in the tubular outer shaft 2 and is returned to the cooling liquid pump 34. The cooling liquid 36 returned to the cooling liquid pump 34 is cooled and then supplied again into the balloon 4. Thus, the cooling liquid pump 34, the cooling liquid passage 38 and the vent tubular shaft 10 form a circulation passage for the cooling liquid 36.

Figure 3:
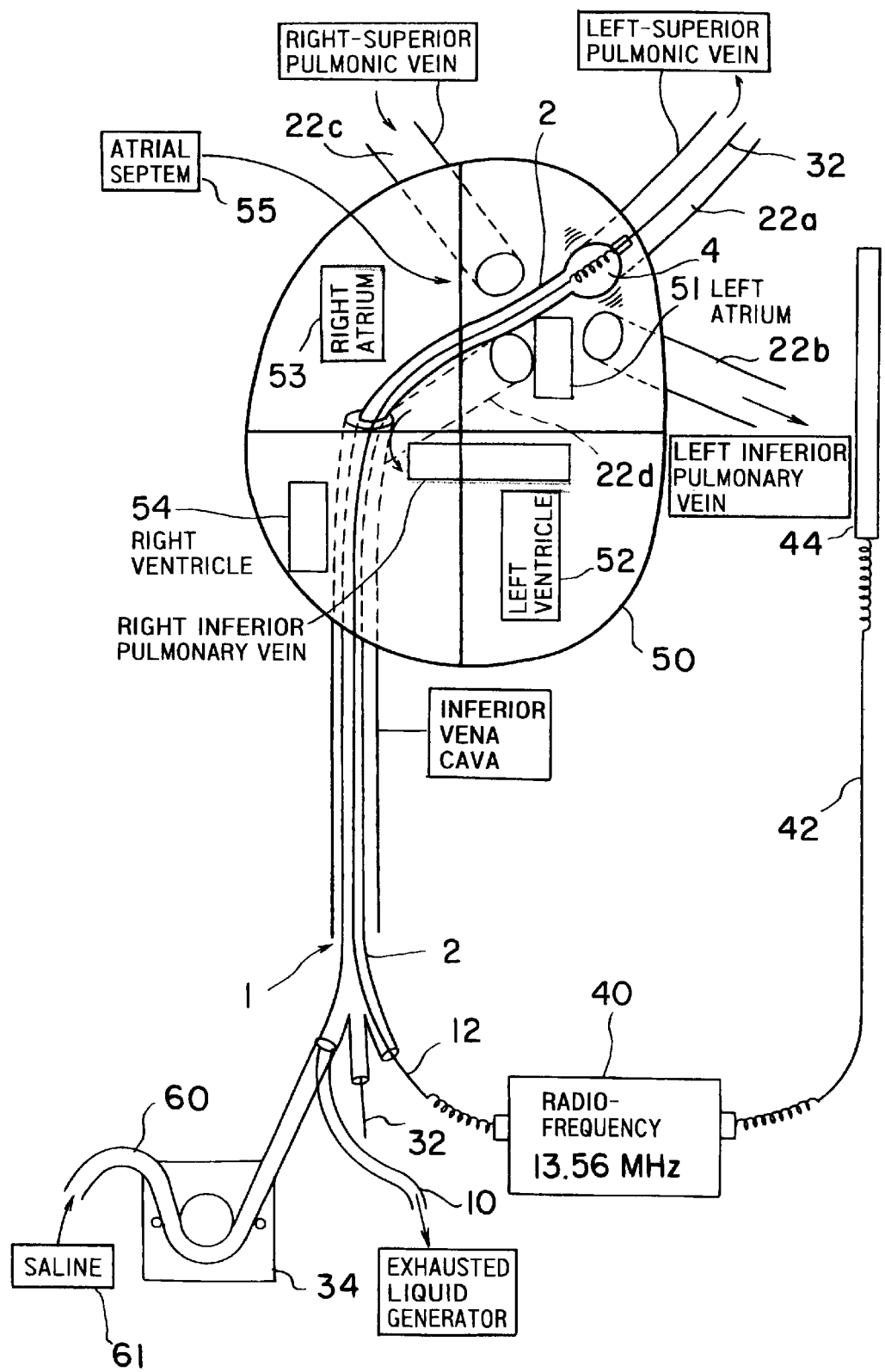
FIG. 3 is a schematic view of assistance in explaining the operation of a balloon catheter for pulmonary vein isolation according to the present invention.

Referring to FIGS. 1 and 3, the lead wire 12 connected to the radio-frequency electrode 8 is extended through the annular space between the tubular outer shaft 2 and the tubular outer shaft 6 and is connected to a radio-frequency generator 40 capable of generating radio-frequency energy of, for example, 13.56 MHz. Since the cooling liquid 36 flows through the cooling liquid passage 38 through which the lead wire 12 is extended, the excessive heating of the tubular outer shaft 2 and the tubular inner shaft 6 by heat generated in the lead wire 12 when energized and the resultant deformation of the tubular outer shaft 2 and the tubular inner shaft 6 can be prevented. A counter electrode 44 placed on the patient's back is connected to the radio-frequency generator 40 by a lead wire 42. The radio-frequency generator 40 supplies radio-frequency power across the radio-frequency electrode 8 and the electric palte 44. For example, radio-frequency power in the range of 200 to 400 W is supplied when the diameter of the balloon 4 is about 2.5 cm.

When the radio-frequency power is supplied across the radio-frequency electrode 8 and the electric plate 44, a portion of the patient's body in contact with the balloon 4 and having a dielectric constant different from that of the balloon 4 is heated and cauterized according to the principle of high-frequency dielectric heating; that is, the annular portion of the junction 26 between the pulmonary vein 22 and the left atrial wall 24, in contact with the balloon 4 is heated and cauterized. As shown in FIG. 1, an annular portion of the junction 26 in contact with the balloon 4 is heated and cauterized. Only the ostium 20 of the pulmonary vein 22, such as the left superior pulmonary vein 22a, is electrically isolated selectively from a left atrium 51 by the circumferential ablation of the junction 26. Even though the radio-frequency generator of a large output capacity is used, heat generated by the lead wire 12 is dissipated in the cooling liquid 36 flowing through the cooling liquid passage 38.

The temperature of the interior of the balloon 14 measured by the thermocouple 14 is indicated on a thermometer 41. The output of radio-frequency energy of the radio-frequency generator 40 is regulated so that the interior of the balloon 4 is maintained at a temperature in the range of 60 to 70° C. Thus, the junction 26 is maintained at an optimum temperature in the range of 60 to 70° C. and hence the carbonization and vaporization of tissues and the formation of thrombi can be prevented.

The radio-frequency generator 40 has a function to monitor the impedance between the radio-frequency electrode 8 and the counter electrode 44. Duration of radio-frequency application time is controlled so that the impedance between the radio-frequency electrode 8 and the counter electrode 44 remains in a predetermined range. Thus, the size of the cauterized portion of the junction 26 can be controlled. The radio-frequency generator 40 is provided with a safety device to stop delivery of radio-frequency energy if the impedance increases sharply.

FIG. 3 shows the balloon catheter 1 in use. The heart 50 has the left atrium 51, the left ventricle 52, the right atrium 53, the right ventricle 54 and the atrial septum 55. The ostium 20 of the four pulmonary veins 22, i.e., the left superior pulmonary vein 22a, the left inferior pulmonary vein 22b, the right superior pulmonary vein 22c and the right inferior pulmonary vein 22d, are formed in the wall of the left atrium 51. First, the guide wire 32 is passed through the inferior vena cava, is made to penetrate through the atrial septum 55 into the left atrium 51 and is inserted deep into the pulmonary vein 22. Subsequently, the guide wire 32 is guided into the tubular outer shaft 2 of the catheter shaft and the balloon catheter 1 is inserted along the guide wire 32 into the inferior vena cave to the ostium of the pulmonary vein 22. The balloon 4 is brought into contact selectively with a portion of the junction 26 around the ostium 20 of one of the four pulmonary veins 22, i.e., the superior pulmonary vein 22a, the left inferior pulmonary vein 22b, the right superior pulmonary vein 22c and the right inferior pulmonary vein 22d.

After the extremity of the balloon catheter 1 has reached the ostium 20 of the pulmonary vein 22, saline 61 is fed through a saline feed line 60 into the balloon 4 by the cooling liquid pump 34 to inflate the balloon 4 in a shape resembling an onion. Consequently, the inflated balloon 4 comes into close contact with a portion of the left atrial wall 24 around the ostium 20. The tubular outer shaft 2 of the catheter shaft is pushed into the inferior vena cava to press the inflated balloon 4 against the left atrial wall 24.

Then, a radio-frequency current of a very high frequency of 13.56 MHz is supplied across the electric plate 44 attached to the patient's back and the radio-frequency electrode 8. While the radio-frequency current is thus supplied, the saline 61 is supplied through the vent tubular shaft 10 into the tubular inner shaft 6 to prevent the temperature of the tubular inner shaft 6 around which the radio-frequency electrode 8 is sound from rising. The annular portion of the junction 26 between the pulmonary vein 22 and the left atrial wall 24, in contact with the balloon 4 is heated and cauterized to isolate the left superior pulmonary vein 22a electrically from the heart 50. Since the cooling liquid 36 is supplied into the balloon 4, the myocandium and the pericandium are cauterized more intensively than the endocardium, so that a transmural necrotic layer can be formed without damaging the endocardium and the formation of thrombi can be avoided.

Since the radio-frequency electrode 8 is coated with a film of an antithrombotic resin, the formation of thrombi can be prevented. Since the balloon 4 is brought into contact with an annular portion of tissues to cauterize the annular portion of the tissues, a region that can be cauterized by one ablation procedure is greater than that can be cauterized by pinpoint ablation. Since the cooling liquid 36 is poured into the tubular outer shaft 2 or the tubular inner shaft 6, the deformation of the tubular outer shaft 2 and the tubular inner shaft 6 by heat generated by the lead wire can be prevented. Since the cooling liquid 36 is poured into the balloon 4 while the radio-frequency current is supplied, the portion of the endocardium in contact with the balloon 4, i.e., the portion of the junction 26 in contact with the balloon 4, is not cauterized excessively and the transmural necrotic layer can be formed around the ostium 20 of the pulmonary vein 22.

A balloon catheter in a second embodiment according to the present invention will be described with reference to FIGS. 2, 4 and 5. The balloon catheter in the second embodiment is similar to the balloon catheter in the first embodiment and hence parts thereof like or corresponding to those the balloon catheter in the first embodiment are denoted by the same reference characters and the description thereof will be omitted.

Figure 2:
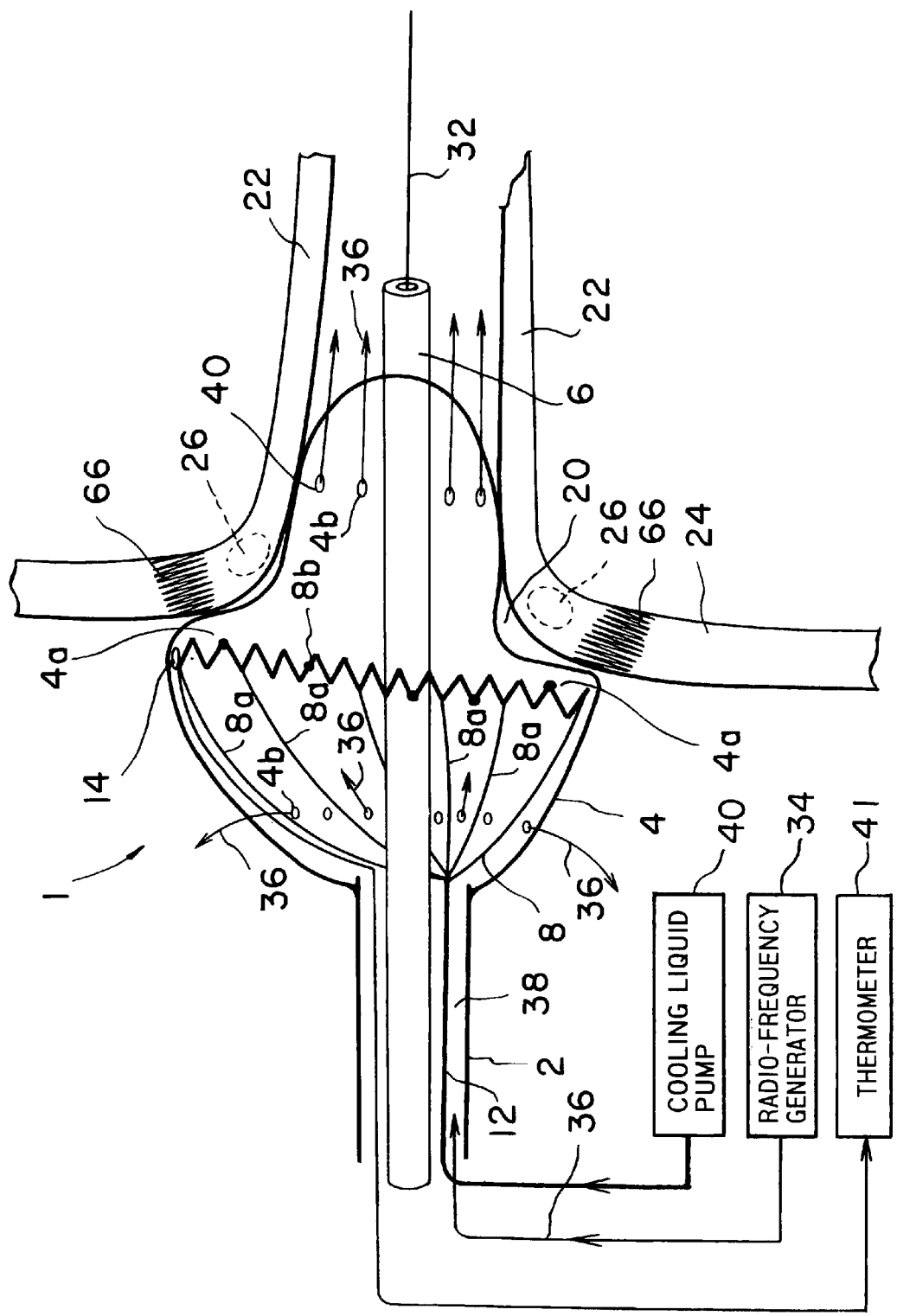
FIG. 2 is schematic sectional view of a balloon catheter for pulmonary vein isolation in a second embodiment according to the present invention in a state where a balloon is inflated.
Figure 4:
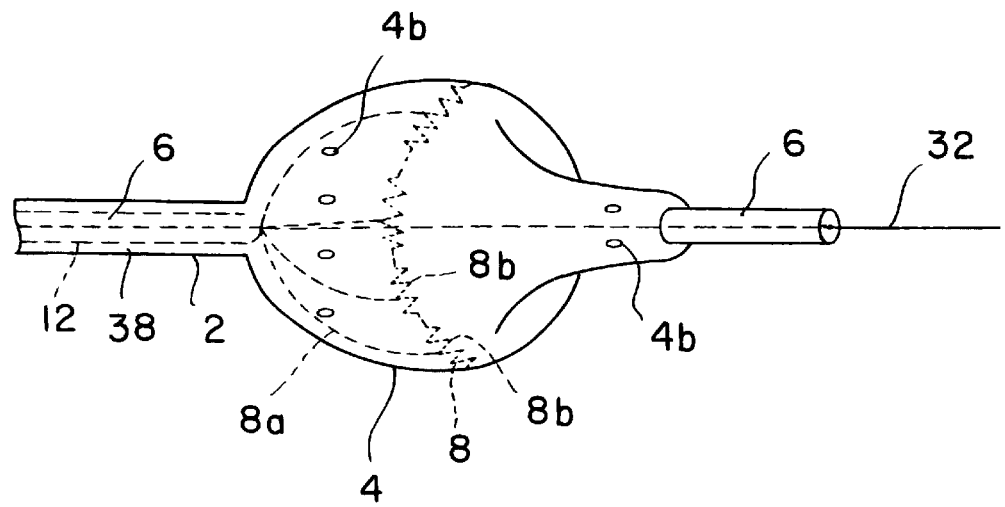
FIG. 4 is a schematic perspective view of a balloon included in the balloon catheter shown in FIG. 2.
Figure 5:
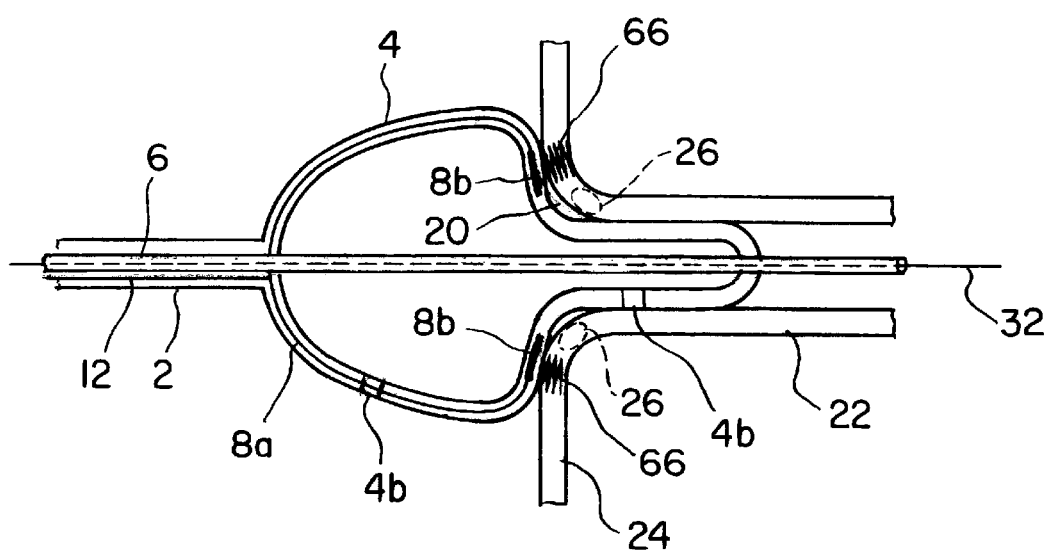
FIG. 5 is a schematic sectional view of a balloon included in the balloon catheter shown in FIG. 2.

Referring to FIGS. 2, 4 and 5 a balloon 4 as inflated has a shape resembling a mushroom having a larger portion on the side of a tubular outer shaft 2 of a catheter shaft. A large portion of the balloon 4 is formed in a double-wall structure consisting of two walls. A radio-frequency electrode 8 is held between the two walls of the large portion of the balloon 4. The radio-frequency electrode 8 has a plurality of branch sections 8a connected to a lead wire 12, and a circular section 8b connected to the extremities of the branch sections 8a. The circular section 8b is formed by bending a wire in a zigzag shape to concentrate radio-frequency power in a portion of the balloon 4 around the circular section 8b. The circular section 8b of the radio-frequency electrode 8 is located in a portion 4a of the large portion of the balloon 4 corresponding to the cap of a mushroom adjacent to a small portion of the balloon 4 corresponding to the stalk of the mushroom.

When the balloon 4 is inflated, the portion 4a of the large portion of the balloon 4 comes into contact with an annular portion 66 of the left atrial wall 24 The annular portion 66 to be cauterized is at a position where the diameter of the entrance 20 is greater than that of the junction 26 at the position shown in FIG. 1. The portion 66 may be cauterized by using the mushroom-shaped balloon 4 after cauterizing the junction 26 by using the onion-shaped balloon 4 shown in FIG. 1.

As shown in FIGS. 2 and 4, the wall of the balloon 4 is provided with a plurality of discharge pores 4b to discharge a cooling liquid 36 into the body. The cooling liquid 36 supplied through a cooling liquid passage 38 into the balloon 4 by a cooling liquid pump 34 is discharged through the discharge pores 4b into the body. Although a tubular shaft corresponding to the vent tubular shaft 10 for circulating the cooling liquid 36 is unnecessary, the balloon catheter 1, similarly to the balloon catheter 1 in the first embodiment, may be provided with a vent tubular shaft 10 and the cooling liquid 36 may be circulated.

When a radio-frequency current is supplied across the radio-frequency electrode 8 and a counter electrode 44 attached to the patient's back, only the annular portion 66 in contact with the balloon 4 is cauterized selectively according to the principle of high-frequency induction dielectric heating. Thus, only the left superior pulmonary vein 22a, for instance, among the pulmonary veins 22 including, in addition to the left superior pulmonary vein 22a, the left inferior pulmonary vein 22b, the right superior pulmonary vein 22c and the right inferior pulmonary vein 22d can be electrically isolated selectively from the heat 50. Since the cooling liquid 36 is supplied into the balloon 4 and is discharged through the discharge pores 4b into the patient's body, the myocandium and the pericandium are cauterized more intensively than the endocardium, so that a transmural necrotic layer can be formed without damaging the endocardium and the formation of thrombi can be avoided.

Since the radio-frequency electrode 8 of the balloon catheter 1 in the second embodiment, similarly to that of the balloon catheter 1 in the first embodiment, is coated with a film of an antithrombotic resin, the formation of thrombi can be prevented. Since the balloon 4 is brought into contact with an annular portion of tissues to cauterize the annular portion of the tissues, a region that can be cauterized by one ablation procedure is greater than that can be cauterized by pinpoint ablation. Since the cooling liquid 36 is supplied through the tubular outer shaft 2 into the balloon 4 and is discharged through the discharge pores 4b into the patient's body, the thermal deformation of the tubular outer shaft 2 and the tubular inner shaft 6 can be prevented. Since the cooling liquid 36 is poured into the balloon 4 while the radio-frequency current is supplied, the portion 66 of the endocardium in contact with the balloon 4 is not cauterized excessively and the transmural necrotic layer can be formed around the ostium 20 of the pulmonary vein 22. Since the radio-frequency electrode 8 is formed in the shape of an umbrella between the walls forming the double-wall structure of the mushroom-shaped balloon 4 and has the branch sections 8a and the circular section 8a, the radio-frequency power can be concentrated in only the portion 66 to be cauterized and the portion 66 can be selectively and effectively cauterized.

A balloon catheter 1 in a third embodiment according to the present invention will be described with reference to FIG. 6. The balloon catheter 1 in the third embodiment is similar to the balloon catheter 1 in the first embodiment and hence parts thereof like or corresponding to those the balloon catheter 1 in the first embodiment are denoted by the same reference characters and the description thereof will be omitted. The balloon catheter 1 in the third embodiment is provided with a cooling system different from that shown in FIG. 1 and is not provided with any member corresponding to the vent tubular shaft 10. The balloon catheter 1 may be provided with either an onion-shaped balloon as shown in FIG. 1 or a mushroom-shaped balloon as shown in FIG. 2.

Figure 6:
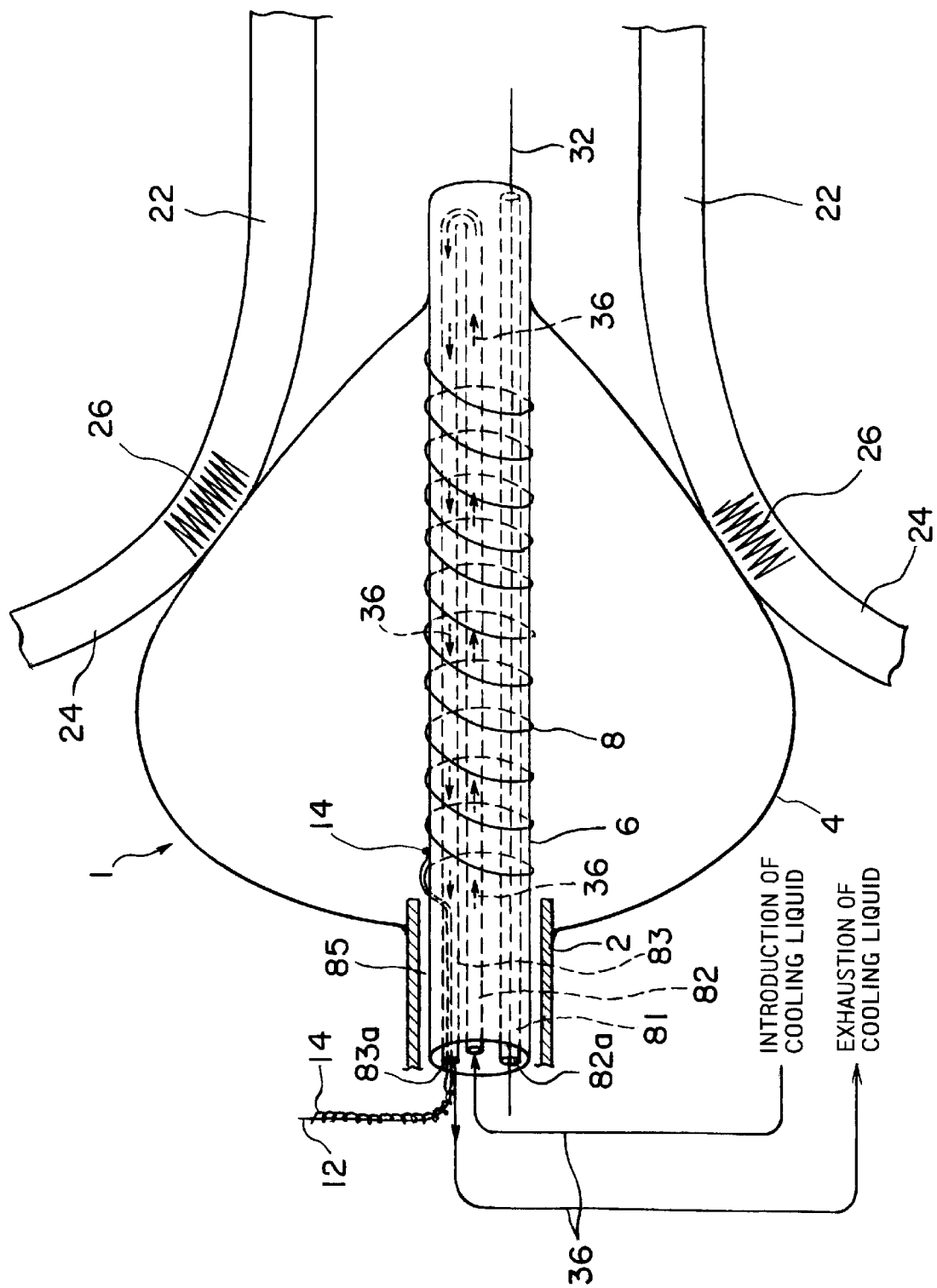
FIG. 6 is a schematic sectional view of a tubular inner shaft of a catheter shaft included in a balloon catheter for pulmonary vein isolation in a third embodiment according to the present invention.

Referring to FIG. 6, an inner shaft 6 is provided with three tubular holes 81, 82 and 83. The tubular hole 81 is extended longitudinally through the inner shaft 6. A guide wire 32 is passed through the tubular hole 81. The tubular holes 82 and 83 are connected by a U-shaped connecting hole in an inner end portion of the inner shaft 6. A cooling liquid 36, such as saline, supplied through an open end 82a of the tubular hole 82 into the tubular hole 82 flows through the U-shaped connecting hole and the tubular hole 83 and is discharged through an open end 83a of the tubular hole 83.

A lead wire 12 and a thermocouple 14 are inserted through the open end 83a into the tubular hole 83 and are led out of the tubular hole 83 onto the outer surface of the inner shaft 6. A radio-frequency electrode 8 is wound in a coil round the inner shaft 6 and is connected to the lead wire 12. As shown in FIG. 6, the lead wire 12 is led through the tubular hole 83 of the inner shaft 6 to the outer surface of a portion of the inner shaft 6 extending in a balloon 4 without pass a region 85 between the inner shaft 6 and a tubular outer shaft 2.

In the balloon catheter 1 in the third embodiment, the U-shaped cooling liquid passage for the cooling liquid 36 is formed in the tubular inner shaft 6 by the tubular holes 82 and 83 to circulate the cooling liquid 36 through the inner shaft 6 by the cooling liquid pump 34. Since the tubular holes 82 and 83 can be formed in a relatively great diameter in the inner shaft 6, the cooling liquid 36 is able to exercise a high cooling ability. Since the cooling liquid 36 flows through the U-shaped cooling liquid passage, the inner shaft 6 can be efficiently cooled.

Thus, even if large radio-frequency power is supplied through the lead wire 12 to the radio-frequency electrode 8, the excessive heating of the inner shaft 6 by heat generated by the led wire 12 extended in the inner shaft 6 and the radio-frequency electrode 8 wound round the inner shaft 6 and the resultant deformation of the inner shaft 6 can be surely prevented.

The cooling methods using the cooling liquid 36 respectively employed in the embodiments illustrated in FIGS. 1, 2 and 6 may be used in combination. The onion-shaped balloon 4 and the mushroom-shaped balloon 4, and the cooling methods illustrated in FIGS. 1, 2 and 6 may be used in various combinations.

The method of supplying the cooling liquid 36 into the shafts 2 and 6 may be a method that supplies the cooling liquid 36 into only the outer shaft 2, a method that supplies the cooling liquid 36 into only the inner shaft 6 or a method that supplies the cooling liquid 36 into both the outer shaft 2 and the inner shaft 6.

As apparent from the foregoing description, according to the present invention, the pulmonary vein can be electrically isolated from the left atrium and most cases of atrial fibrillation can be cured by effectively reducing atrial premature beat, which is a triggering factor of atrial fibrillation, by a nonsurgivcal treatment. Since the balloon can be brought into local contact with a predetermined portion of a single pulmonary vein near the pulmonary vein ostium, predetermined portions around the pulmonary veins can be individually cauterized without requiring extracorporeal circulation. Since only the predetermined portion around the pulmonary vein ostium can be locally cauterized without cauterizing other portions of the pulmonary vein, a complication of pulmonary hypertension due to the restenosis of the pulmonary vein can be avoided. The thermal deformation of the outer and the inner shaft of the catheter shaft can be prevented by supplying the cooling liquid into the catheter shaft or the balloon.

Although the invention has been described in its preferred embodiments with a certain degree of particularity, obviously many changes and variations are possible therein. It is therefore to be understood that the present invention may be practiced otherwise than as specifically described herein without departing from the scope and spirit thereof.

What is claimed is:

1. A balloon catheter for pulmonary vein isolation comprising:
   a catheter shaft consisting of a tubular outer shaft and a tubular inner shaft;
   an inflatable balloon capable of coming into contact with a predetermined annular portion of a pulmonary vein ostium when inflated and having one end portion connected to an extremity of the tubular outer shaft and the other end portion connected to an extremity of the tubular inner shaft;
   a radio-frequency electrode paired with an electric plate placed on a surface of a patient's body to transmit radio-frequency power, and placed in a wall forming the balloon or in the balloon;
   a lead wire connected to the radio-frequency electrode;
   a cooling means for pouring cooling liquid to cool respective interior of the catheter shaft and the balloon; and
   a temperature sensor for measuring temperature in the balloon.

2. The balloon catheter for pulmonary vein isolation according to claim 1, wherein the balloon as inflated has a shape resembling an onion having a larger portion on the side of the tubular outer shaft of the catheter shaft.

3. The balloon catheter for pulmonary vein isolation according to claim 1, wherein the balloon as inflated has a shape resembling a mushroom having a large portion on the side of the tubular outer shaft of the catheter shaft.

4. The balloon catheter for pulmonary vein isolation according to claim 1, wherein the radio-frequency electrode is wound round the tubular inner shaft of the catheter shaft.

5. The balloon catheter for pulmonary vein isolation according to claim 1, wherein the radio-frequency electrode is formed in a circular shape on an inner surface of the wall of the balloon so as to be located close to the predetermined portion when the balloon is inflated.

6. The balloon catheter for pulmonary vein isolation according to claim 1, wherein the predetermined portion is a junction between a pulmonary vein and a left atrial wall.

7. The balloon catheter for pulmonary vein isolation according to claim 1, wherein the predetermined portion is a portion of a left atrial wall around a pulmonary vein.

8. The balloon catheter for pulmonary vein isolation according to claim 1, wherein the cooling means circulates cooling liquid.

9. The balloon catheter for pulmonary vein isolation according to claim 1, wherein a U-shaped cooling liquid passage through which the cooling liquid can be circulated is formed in the tubular inner shaft of the catheter shaft.

10. The balloon catheter for pulmonary vein isolation according to claim 1, wherein radio-frequency power is supplied to the radio-frequency electrode to heat the balloon at a predetermined temperature and temperature of the balloon is monitored by means of the temperature sensor.

11. The balloon catheter for pulmonary vein isolation according to claim 1, wherein radio-frequency power is supplied to the radio-frequency electrode so that impedance between the radio-frequency electrode and the counter electrode is in a predetermined impedance range and the impedance between the radio-frequency electrode and the counter electrode is monitored.

12. The balloon catheter for pulmonary vein isolation according to claim 1, wherein the tubular outer shaft, the tubular inner shaft and the balloon are formed of an antithrombotic resin and have smooth surfaces, respectively.

* * * * *